US00PP09419P

United States Patent [19]

Olesen et al.

[11] Patent Number: Plant 9,419

[45] Date of Patent: Jan. 9, 1996

[54] MINIATURE ROSE PLANT NAMED 'POULIT'

[75] Inventors: Mogens N. Olesen; Pernille Olesen, both of Fredensborg, Denmark

[73] Assignee: Weeks Wholesale Rose Grower, Inc., Upland, Calif.

[21] Appl. No.: 367,812

[22] Filed: Jan. 3, 1995

[51] Int. Cl.[6] ..... A01H 5/00

[52] U.S. Cl. ..... Plt./9

[58] Field of Search ..... Plt./7.1, 9

*Primary Examiner*—Howard J. Locker

*Attorney, Agent, or Firm*—Christie, Parker & Hale

[57] ABSTRACT

A new variety of miniature rose suitable for garden decoration, having flowers of light pink coloration.

1 Drawing Sheet

BACKGROUND OF THE INVENTION

This invention relates to a new and distinct variety of miniature rose. The varietal denomination of the new variety is 'Poulit'. The plant is a compact miniature bush cultivated for outdoor garden decoration. It has 'Egeskov' as its seed parent and an unnamed, undisseminated seedling as its pollen parent.

SUMMARY OF THE INVENTION

Among the features which distinguish the new variety from other presently available and known commercial rose cultivars are the following combination of characteristics: its very abundant bloom, its low compact rounded bush habit, its very full petalage flowers of old garden rose form, its low pistil count, and its blush color on the stipules. 'Poulit' may be asexually propagated by cuttings, budding, or grafting.

Asexual reproduction of the new variety as performed by budding in Kern County and Upland, Calif., shows that the foregoing and other distinguishing characteristics come true to form and are established and transmitted through succeeding propagations.

COMPARISON WITH PARENT VARIETIES

The new rose may be distinguished from its seed parent, 'Egeskov' by the following combination of characteristics: whereas 'Poulit' is classified as a miniature with proportionately small flowers, foliage and plant habit, 'Egeskov' is classified as a Floribunda with significantly larger flowers, foliage and plant habit. Whereas 'Egeskov' bears flowers of a very light pink to cream coloration, the new seedling bears flowers of a significantly darker pink coloration.

The new variety may be distinguished from its pollen parent, an undisseminated seedling, by the following combination of characteristics: whereas 'Poulit' bears full petaled flowers of a pink coloration, the seedling pollen parent bears flowers with significantly lower petalage and light cream to pink coloration. The seedling pollen plant has dark green foliage, whereas the new variety has foliage of a significantly lighter coloration.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

FLOWER

The new variety bears its flowers sometimes singly, but usually three or more per stem. Flowers are borne in irregular, rounded clusters on short stems (about 5 to about 12 cm), for the class. Outdoors the plant blooms very abundantly and nearly continuously during the growing season. The flowers have a light fragrance of fresh cut apples.

BUD

The peduncle is of normal length for the class (about 3 to about 4 cm), of normal caliper, and usually erect. It is usually smooth with some stipitate glands. Peduncle color is between 146B and 137D, sometimes very lightly suffused with near 184C.

Before the calyx breaks, the bud is of medium size for the class (about 0.8 to about 1.3 cm in diameter at the widest point), short to medium in length (about 2 to about 2.5 cm), and pointed to ovoid in shape. The surface of the bud is very smooth bearing a very light glandular bloom, usually with slender entire foliaceous parts extending beyond the tip of the bud equal to about ½ or more of its length. Bud color is between 146C and 137C.

The inner surface of the sepals is covered with fine wooly tomentum; sepal margins are lined with some stipitate glands and many hairs.

As the petals open, the bud is of medium size for the class (about 1 to about 1.4 cm in diameter at the widest point), short to medium in length (about 1.7 to about 2 cm), and somewhat flat-topped to globular in form. The color of the under surface of the newly opened petals is between 52D and 55C. The color of the upper surface of the newly opened petals is between 49B and 55C. At the very base where the petals attach is a small-to-medium sized zone of near 4C. The bud opens up well and is not prevented from opening by wet, cold, hot or dry weather.

BLOOM

When fully open, the bloom is of medium size for the class, ranging from about 3.5 to about 5 cm in diameter. Petalage is very double with about 37 to 45 petals and about 5 to 8 petaloids arranged regularly. When partially open, the bloom form is moderately flat-to-cupped and the petals are tightly cupped to imbricated with petal edges somewhat rolled outward. When fully open, the bloom form is more cupped and full and the petals are more loosely cupped-to-flat with petal edges somewhat rolled outward.

PETALS

The petals are of good substance and medium thickness, with upper and under surfaces slightly satiny. The outer petals are broadly oval to obovate in shape with rounded apices. The intermediate petals are moderately obovate in shape with rounded to slightly mucronate apices. The inner petals are very narrowly obovate in shape with mucronate-to-acute apices.

NEWLY OPENED FLOWER

The under surface of the outer, intermediate and inner petals is between 55C and 55B. The upper surface of the outer, intermediate and inner petals is between 55D and 56A. At the very base where the petals attach is a small to medium sized zone of near 4D.

The general tonality of the newly opened flower is between 55D and 56A.

THREE DAY OLD FLOWER

The under and upper surface of the outer and inner petals is between 56D and 56C. At the very base where the petals attach is a small zone of near 155A.

The general tonality of the three day old flower is between 56D and 56C.

The petals usually drop off the spent blooms cleanly and are not particularly affected by cold, hot, wet, or dry weather.

In September in Upland, Calif., blooms on the bush growing outdoors generally last from four or more days. Cut roses grown outdoors and kept at normal indoor living temperatures generally last four or more days.

MALE REPRODUCTIVE ORGANS

Stamens are few to average in number and are arranged regularly about the pistils; a few are mixed with petaloids or tucked in the calyx. The filaments are of irregular length, most with anthers. The anthers are small to medium sized for the class and all open approximately at the same time. Anther color is near 16B when immature and near 164A at maturity. Pollen is sparse and near 4C in color.

FEMALE REPRODUCTIVE ORGANS

Pistils are very few in number (approximately 18). The styles are of medium length, uneven, of normal caliper, and loosely bunched. Stigma color is near 16D. Style color is near 16D sometimes suffused with 50C. Ovaries are usually all enclosed in the calyx.

Hips are globular to nearly round in form, and heavily suffused with near 169B in color when ripe. The hip surface is very smooth with moderately thick fleshy walls. The sepals fall away quickly. Seeds are few in number (approximately 6 to 8), and small in size.

FOLIAGE

The compound leaves are usually comprised of three to five, and sometimes seven, leaflets and are borne abundantly. The leaves are of medium size for the class (about 4 to about 7 cm in length and about 3 to about 4.5 cm in width at the widest point), normal to heavy in texture, and somewhat semi-glossy to matte in finish. The leaflets are of medium size for the class (about 1.4 to about 2.2 cm in length and about 1 to about 1.5 cm in width at the widest point), shaped somewhat round to oval with acute apices and rounded bases. Margins are usually serrate.

The upper surface of the mature leaf is between 137A and 138B. The under surface of the mature leaf is between 138B and 191B. The upper surface of the young leaf is between 146C and 137C, sometimes lightly suffused with near 184B. The under surface of the young leaf is near 146D, sometimes lightly suffused with near 184C.

The rachis is light to normal in caliper and usually smooth and grooved with few hairs and stipitate glands on the edges of the upper side. The under side of the rachis is smooth with few hairs and stipitate glands and 1 to 2 very small prickles.

The stipules are medium to long, and medium width with medium to long straight points that usually turn out at an angle of more than 45 degrees. The under and upper side of the stipules at the point of attachment to the stem are blushed with near 184C.

The plant displays an above average degree of resistance to powdery mildew and rust as compared to other commercial varieties grown under comparable conditions in Upland, Calif.

GROWTH

The plant has a dwarf bushy compact rounded habit of low height (about 30 to 40 cm in height and spread at the widest point), with very full branching. It displays moderately vigorous growth and the canes are of light to medium caliper for the class.

The color of the major stems is between 138A and 147B. They bear few medium to large prickles for the class which are medium length to long (about 0.4 to about 0.6 cm). The prickles are very straight with a medium length narrow base; prickle color is between 175C and 180C. The major stems bear no small prickles.

The color of the branches is between 146C and 137C. They bear some medium to large prickles for the class which are medium to long (about 0.4 to about 0.6 cm). The prickles are very straight with a medium length narrow base; prickle color is between 175C and 180C. The branches bear no small prickles.

The color of the new shoots is between 146B and 137D often lightly suffused with near 184C. They bear some medium to large prickles for the class which are medium length to long (about 0.4 to about 0.6 cm). The prickles are very straight with a medium length narrow base; prickle color is near 184D. The new shoots bear few small prickles.

We claim:

1. A new and distinct variety of miniature rose plant substantially as described and illustrated herein.

* * * * *

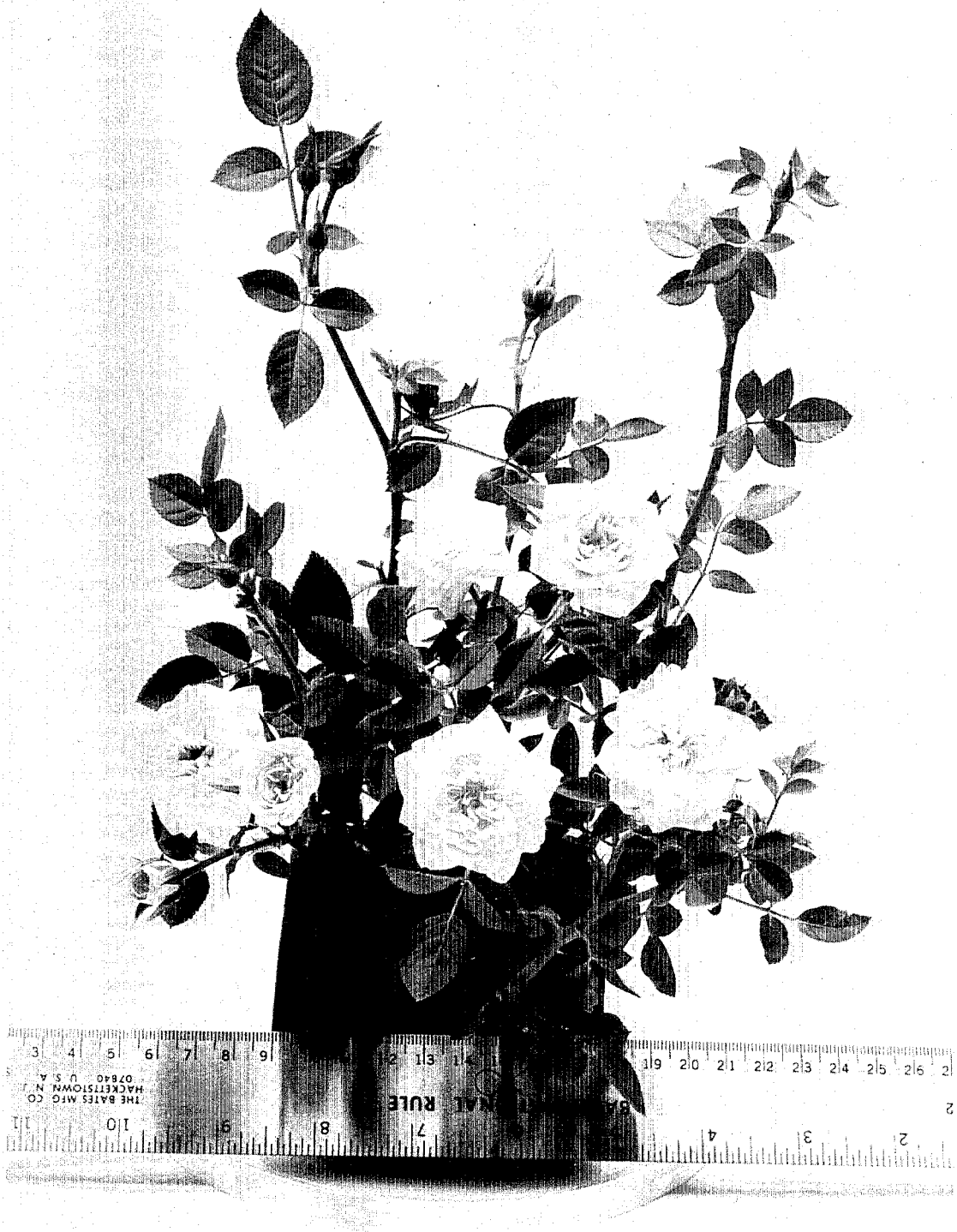
THE BATES MFG CO
HACKETTSTOWN N.J.
07840 U.S.A.